United States Patent
Vodyanoy et al.

(10) Patent No.: US 6,788,071 B2
(45) Date of Patent: Sep. 7, 2004

(54) METHOD AND APPARATUS FOR GENERATING A VOLTAGE ACROSS A MEMBRANE

(75) Inventors: Vitaly J. Vodyanoy, Auburn, AL (US);
Solomon Yilma, Auburn, AL (US);
Ting To Lo, Auburn, AL (US);
Alexander Samoylov, Auburn, AL (US)

(73) Assignee: Auburn University, Auburn, AL (US)

( * ) Notice: Subject to any disclaimer, the term of this patent is extended or adjusted under 35 U.S.C. 154(b) by 73 days.

(21) Appl. No.: 10/201,746

(22) Filed: Jul. 23, 2002

(65) Prior Publication Data

US 2003/0020489 A1 Jan. 30, 2003

Related U.S. Application Data

(60) Provisional application No. 60/307,406, filed on Jul. 24, 2001.

(51) Int. Cl.[7] ................................................ G01R 27/02
(52) U.S. Cl. ........................................ 324/603; 324/602
(58) Field of Search ................................. 324/602–609, 324/750–753, 765, 770, 158.1, 71.1, 522

(56) References Cited

U.S. PATENT DOCUMENTS 4,294,091 A    10/1981  Prunbauer 5,774,223 A  *  6/1998  Urakami et al. ............. 356/394
6,288,527 B1 *  9/2001  Sugihara et al. ............ 324/71.1

FOREIGN PATENT DOCUMENTS

JP           62063823 A  *  3/1987  ............. G01J/1/00

OTHER PUBLICATIONS

Korchev, Yurl E. Gorelik, Julia, LAB, Max J., Sviderskaya, Elena V., Johnston, Caroline L., Coombes, Charles R., Vodyanoy, Igor, Edwards, Christopher R.W.; "Cell Volume Measurement Using Scanning Ion Conductance Microscopy"; Biophysical Journal; Jan. 2000; pp. 451–457; vol. 78.
Pathirana, Suram, Neely, William C., Myers, Lawrence J., Vodyanoy, Vitaly, "Interaction of Valinomycin and Stearic Acid in Monolayers"; Langmuir, 1992; pp. 1984–1987; vol. 8, No. 8.
Vodyanoy, Vitaly; "Olfactory Sensor"; IEEE Engineering in Medicine & Biology Society 10th Annual International Conference; 1988; pp. 0997–0998.

* cited by examiner

*Primary Examiner*—Minh Chau
(74) *Attorney, Agent, or Firm*—Gardner Groff, PC

(57) ABSTRACT

A method and apparatus for generating a transmembrane voltage, including a semiconductive substrate having a surface for receiving a membrane thereon, and a light source for illuminating at least a portion of the semiconductive substrate. Measurement of current through the membrane addresses ion channels through the membrane at the location illuminated by the light source.

16 Claims, 4 Drawing Sheets

METHOD AND APPARATUS FOR GENERATING A VOLTAGE ACROSS A MEMBRANE

CROSS-REFERENCE TO RELATED APPLICATION

This application claims the benefit of U.S. Provisional Patent Application Serial No. 60/307,406, filed Jul. 24, 2001, which is hereby incorporated herein by reference in its entirety for all purposes.

FIELD OF THE INVENTION

This invention relates generally to the field of membrane study, biosensor/biomembrane development and manufacture, and nano-scale photovoltaics. The invention relates more particularly to a method and apparatus for photoelectrically applying a voltage across a membrane for membrane channel addressing, power supply and switching for nanodevices, nano-scale signal transmission and other applications.

BACKGROUND OF THE INVENTION

The application of a voltage across a biological or synthetic membrane can be utilized in a variety of applications. For example, application of a localized voltage across a membrane can be used to address or map biological structures such as ion channels and/or to detect binding events at a channel. An amphotericin B ion channel within a supporting membrane, for example, is held open by a cholesterol molecule that zips the amphotericin molecules together in a channel-forming configuration, allowing ion transport through the membrane. When a free analyte binds to the associated antibodies of the amphotericin molecules, the cholesterol molecule is displaced and the channel is unzipped, resulting in disaggregation and closing of the channel, thereby blocking ion transport across the membrane.

The presence or absence of such ion channels or carriers in a membrane can act as a molecular switching element that converts a binding event into an electrical signal, functioning as a transducer in a biosensor or nanodevice. For example, in a membrane in which a molecular channel or switch is held open when a specific analyte is bound, ion transport through the membrane is permitted when the analyte is bound, but is blocked when the analyte is not bound. If a voltage is applied across the membrane, a current pulse will be observed if ion transport occurs through the membrane, indicating an open channel and thus the presence of a binding event. Conversely, if a voltage is applied across the membrane and no current is observed (i.e., no ion transport through the membrane), a closed channel (and thus the absence of a binding event) is indicated.

The very small scale of the membranes and the molecules forming ion channel and ion carrier molecular switches under investigation (commonly on the order of about 100 Angstroms), as well as the relatively high density of ion channels on a substrate renders the addressing of these channels very difficult using known techniques. One conventional solution for the addressing of biological structures such as ion channels would be to make electrical connections to all or to many of these molecular switches. The applied voltage and responses of individual addresses on a substrate such as a silicon wafer surface could be scanned with the aid of computerized circuitry. However, the resolution of known addressable electrodes is poor, and manufacturing of an electrode system on the substrate surface would likely prove difficult and expensive. Also, voltage applied to a membrane in an electrolytic solution is typically conducted through the electrolyte along the membrane surface, rendering it difficult or impossible to address or map a specific location on the membrane.

It is also known to utilize a scanning ion conductance microscope to image the topography of soft non-conducting surfaces covered with electrolytes by maintaining a micropipette probe at a constant conductance distance from the surface. This method can sample and image the local ion currents above the surface by scanning with a micropipette probe in a plane located at a constant distance above the surface. Multiple micropipettes mounted in a multi-barrel head and containing various ion specific electrodes allow simultaneous scanning for different ion currents. The resolution of this method, however, is low and the method is tedious and costly.

Scanning ion conductance microscopy (SICM) techniques for assessing the volume of living cells allow quantitative, high-resolution characterization of the dynamic changes in cell volume while retaining the cell's functionality. This technique is reportedly capable of measuring a widerange of volumes. The volume of small cellular structures such as lamelopodia, dendrites, processes, or microvilli, can purportedly be measured with $2.5 \times 10^{20}$ resolution. The sensitive probe of this method is a glass micropipette filled with electrolyte and connected to a high-impedance head-stage amplifier that is mounted on a computer-controlled three-axis translation stage. This method, however, is also unwieldy and costly.

The application of a voltage across a membrane may also find application in energy delivery, switching and/or signal transmission for nano-scale devices ("nanodevices"), and in other fields of endeavor. To date, however, these areas of technology have not been developed to a significant extent, likely due at least in part to the lack of suitable methods and apparatus for locationally precise voltage application.

Thus, it can be seen that needs exist for improved methods and apparatus for applying a voltage across a membrane. It is to the provision of improved apparatus and methods meeting this and other needs that the present invention is primarily directed.

SUMMARY OF THE INVENTION

The present invention provides an improved apparatus and method for applying a voltage across a membrane. Example embodiments of the apparatus and method of the present invention enable precise locational control of the point of application of voltage across a membrane, providing improved addressing of biological structures such as ion channels and improved detection of binding events at a channel. In other embodiments, the method and apparatus of the present invention provide photoelectric power supply, microswitching, energy transmission and/or signal transmission suitable for use in connection with nanodevices including without limitation: nanomotors, nanoswitches, nanotranslators and/or micropositioners.

In one embodiment, the method and apparatus of the present invention uses a photoelectric method to generate a voltage across a membrane applied to a substrate, in which the transmembrane voltage is used to address biological structures such as ion channels or molecular switches on the substrate surface. Application of light on a semiconductor/electrolyte-liquid interface generates an electrical charge gradient due to the photovoltaic effect. The electrochemical gradient drives electric current carriers (electrons and/or ions) through the interface. When a membrane with open ion channels is applied to the substrate at the semiconductor/liquid interface, the current induced by the light flows relatively freely through the open channels, resulting in a relatively large induced current. When the channels are closed or blocked, the current through the membrane is small or non-existent.

By scanning the substrate surface with a narrowly-focused laser beam or other light source and monitoring the current induced by the application of light at each location along the scanned path, channel opening events are observed and the electrical topography of the surface can be addressed and recorded. The laser beam illuminates a small portion of the substrate/liquid interface, creating an electrochemical gradient that drives current through any open ion channel (or small group of channels) located at the illuminated position. By sequentially moving or continuously scanning the point of illumination with the laser beam across the surface, the electrical pattern and topography of the substrate is generated and the ion channels are mapped. In example embodiments, this method of photoelectrically addressing biological structures such as ion channel switches offers the advantages of high resolution of the electrical topography of the surfaces, low cost and simplicity.

In one aspect, the invention is a method of generating a voltage across a membrane. The method preferably includes applying a membrane to a semiconductive substrate, and illuminating at least a portion of the semiconductive substrate with a light source.

In another aspect, the invention is a method of observing molecular channel opening events and addressing the electrical topography of a membrane. The method preferably includes the steps of providing a semiconductive substrate having a membrane deposited thereon in contact with an electrolytic solution to form a semiconductor/liquid interface, scanning successive portions of the semiconductive substrate with a light source to generate a localized electrical charge gradient at a location on the semiconductor/liquid interface, and measuring an electrical current through the membrane.

In yet another aspect, the invention is an apparatus for generating a transmembrane voltage. The apparatus preferably includes a semiconductive substrate having a surface for receiving a membrane thereon, and a light source for illuminating at least a portion of the semiconductive substrate.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are explanatory of example embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
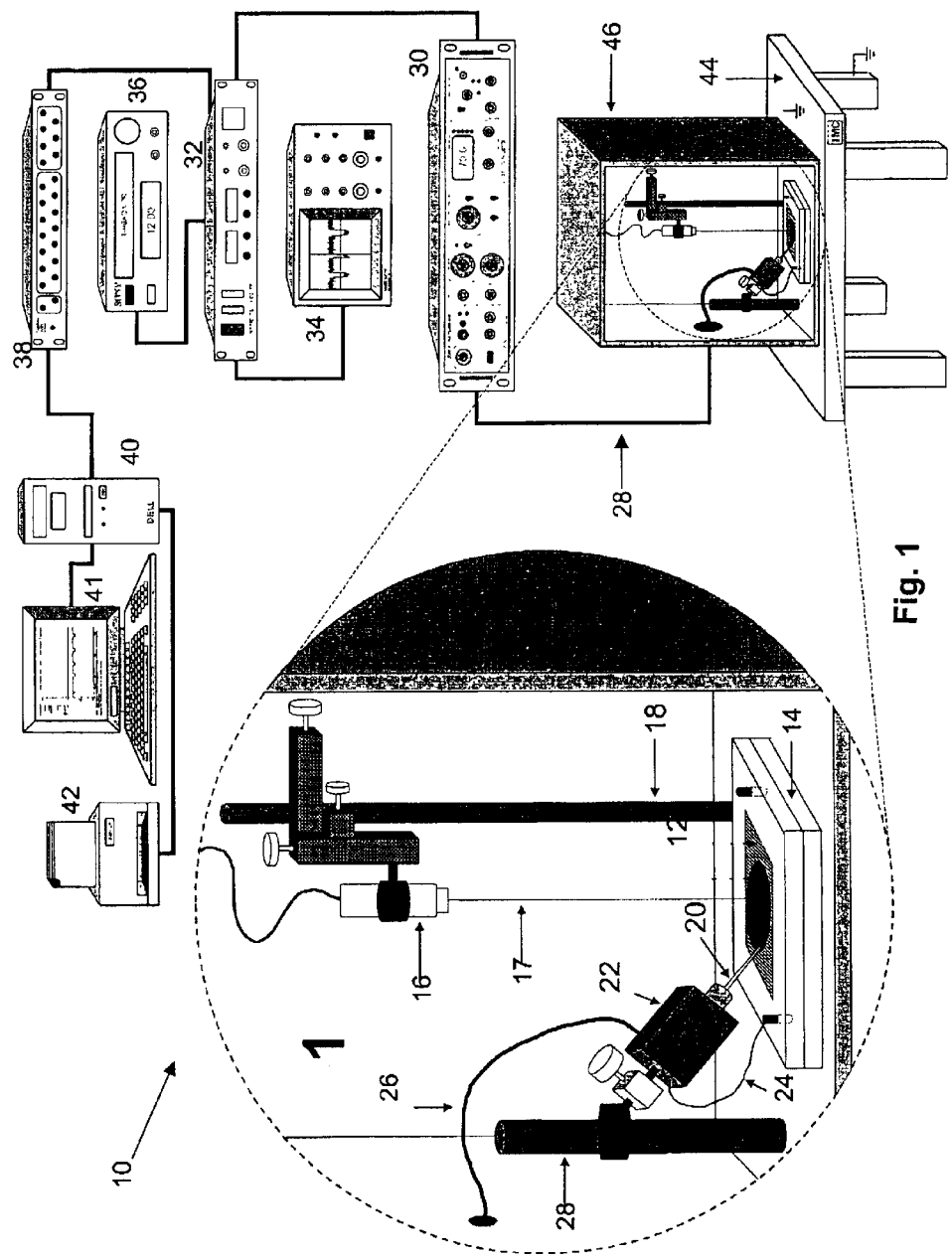
FIG. 1 shows an apparatus for applying a voltage across a membrane according to an example embodiment of the present invention.

An example embodiment of an apparatus 10 for generating a voltage across a membrane is shown in FIG. 1. A semiconductive substrate 12, such as a silicon wafer is mounted to a base or carrier 14. The apparatus 10 further comprises a light source 16, such as for example a narrow beam laser, positioned and oriented for illumination of at least a portion of the semiconductive substrate 12. A 0.9 mW focusable diode, 635 nm diode laser has been found to produce acceptable results in a prototype apparatus constructed by the inventors. The light source 16 preferably directs a narrowly focused beam 17 of light onto the semiconductive substrate 12. The apparatus 10 preferably further includes a stand or support structure 18 for supporting the light source 16 in a selected position relative to the semiconductive substrate 12. The stand 18 is preferably user-adjustable in at least one direction.

The base or carrier 14 preferably includes a two-dimensional (x-y) translational mechanism such as a piezoelectric driver, a turntable, or other means for moving the semiconductive substrate 12 relative to the point of illumination of the light source 16 in a selectively controllable manner. Alternatively or additionally, the light source 16 is translationally mounted, and/or one or more movable mirrors or lenses are provided between the light source and the semiconductive substrate 12, to move the point of illumination of the light source relative to the semiconductive substrate. A manual or automated control system is preferably included to enable a user to selectively scan the light source 16 to illuminate successive portions of the semiconductive substrate 12. For example, a computer-controlled control system can be programmed to scan the point of illumination of the light source 16 back and forth across the semiconductive substrate 12 in a direction parallel to a first axis of a rectangular coordinate system (the "x-direction"), and step incrementally along a second axis (the "y-direction"), perpendicular to the first axis, after each scan; thereby scanning all or a substantial portion of the surface of the semiconductive substrate 12.

The apparatus 10 preferably further comprises at least one electrode 20 for measuring an induced current, as will be described further below. The head stage 22 of the electrode is preferably electrically grounded by a ground wire 24, as shown. A relay wire 26 transmits a signal from the electrode 20 to a monitoring and/or recording system. An electrode support 28 is preferably provided to support the electrode 20 and associated equipment in a selected position. In the depicted embodiment, the monitoring and/or recording system includes a signal amplifier 30, such as an Axopatch 200B patch-clamp amplifier; an analog/digital converter 32; an oscilloscope 34; a recording device 36, such as a VHS video cassette recorder (VCR); and an interface box 38, such as a Digidata 1200A digital interface box. The monitoring and/or recording system preferably further comprises one or more computer(s) 40, preferably including a video monitor 41, for receiving and transmitting data, and/or one or more printer(s) 42 for printing data and reports related thereto. The components of the monitoring and/or recording system can be separate, individual components, or two or more of the components can be combined into an integral component. Separate components can be connected by hard-wiring or by wireless communication.

All or a portion of the apparatus 10 of the present invention can be supported on an isolation table 44 or other vibration-isolating support to prevent external vibration from interfering with the operation thereof. Also, the apparatus 10 or portions thereof can be enclosed in a Faraday box 46 or other shielding enclosure to block interference from external electrical noise.

Figure 2:
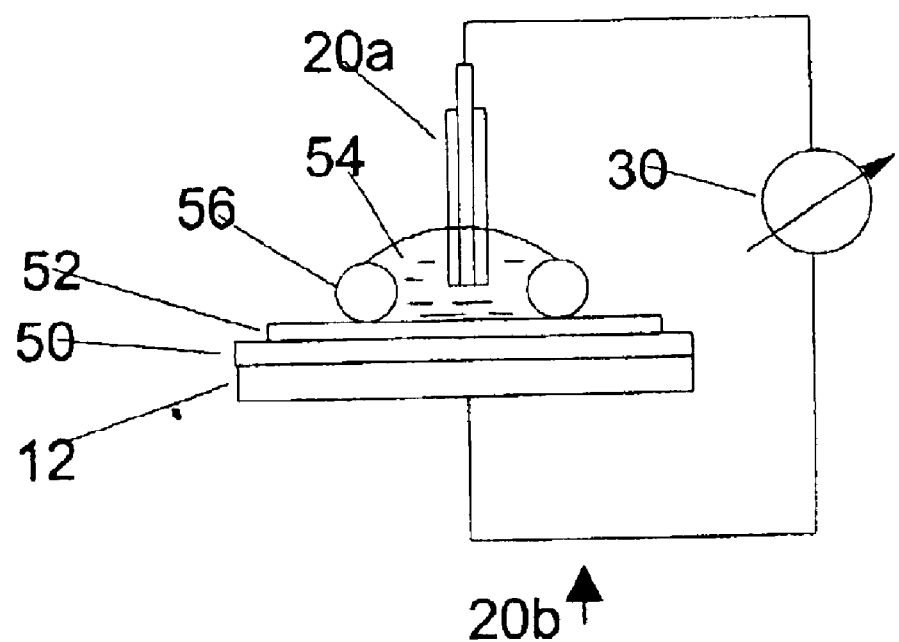
FIG. 2 shows a detailed view of a membrane sample on a substrate according to an example embodiment of the present invention.

FIG. 2 shows the semiconductive substrate 12 and associated elements in greater detail. The semiconductive substrate 12 preferably comprises a porous material such as a porous silicon, having a surface 50 defining a multiplicity of nanopores (approx. 7 nm). It has been found that a porous semiconductive surface generally allows a greater voltage difference to be generated across a membrane applied thereto than does a non-porous surface.

A membrane 52 is preferably applied to the porous surface 50 of the semiconductive substrate 12. The membrane is preferably a biological or synthetic membrane, typically having a thickness on the order of about 100 Angstrom. In example embodiments, the membrane comprises a two-monolayer membrane of lipid vesicles, and can be applied to the substrate using the Langmuir-Blodgett (LB) technique or other suitable membrane formation technique.

An electrolytic solution 54, such as potassium chloride (KCl), is applied to the semiconductive substrate 12, over the membrane 52. An O-ring 56 or other barrier is preferably provided for containing a quantity of the electrolytic solution 54 on the semiconductive substrate 12 over the membrane 52. The tip of a first electrode 20a, such as a silver/silver chloride (Ag/AgCl) electrode, is immersed in electrically conductive contact into the electrolytic solution 54, and a second electrode 20b is in electrical contact with the back of the semiconductive substrate 12.

Figure 3:
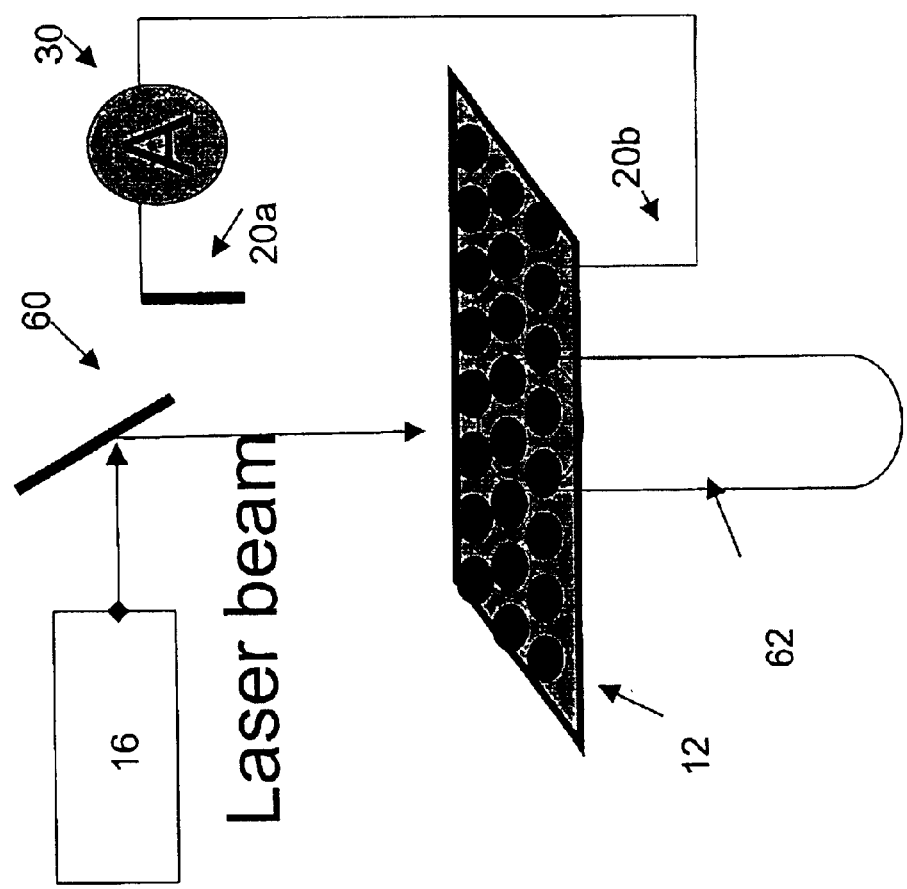
FIG. 3 schematically shows a method of photoelectrically addressing a membrane, according to an example embodiment of the present invention.

FIG. 3 schematically depicts a method of generating a voltage across a membrane according to an example embodiment of the invention. A light source such as laser 16 illuminates a selected portion of a semiconductive substrate 12 having a membrane 52 applied thereon. As the laser beam illuminates the semiconductor/electrolyte interface, an electrochemical gradient is created by the photovoltaic effect, thereby generating a voltage across the membrane.

In one application of the present invention, the voltage generated across the membrane is used to address ion channels of the membrane and/or to generate an image of the electrical pattern and topography of the substrate. A mirror 60 interposed between the light source 16 and the semiconductive substrate 12, and/or a piezoelectric transport table 62 is/are controlled to scan the area of illumination of the light source across all or a portion of the semiconductive substrate having the membrane applied thereto. The generated electrochemical gradient induces an electrical current through the membrane at the location of any open ion channels. The electrodes 20a, 20b allow the detection and measurement of this current and communicate a signal to the monitoring and/or recording system for observation and further analysis.

In other applications of the invention, the voltage generated across the membrane is used as a power source for a nanodevice. For example, a remotely located laser or other light source is directed to generate a local voltage used to power a nano-scale motor, positioner, translator or the like. The light source can be constant to generate a DC-like power source, or can be pulsed at a selected frequency to generate an AC-like power source. The method and apparatus of the present invention can also be used in signal transmission applications, using pulsed application of light to generate an electrical signal. In still other applications, the apparatus of the present invention functions as a nano-scale switch, by allowing the selective passage or blocking of an electrical current depending upon the open/closed state of one or more ion channels in the membrane, which can be selectively controlled by inducing a binding event.

Figure 4:
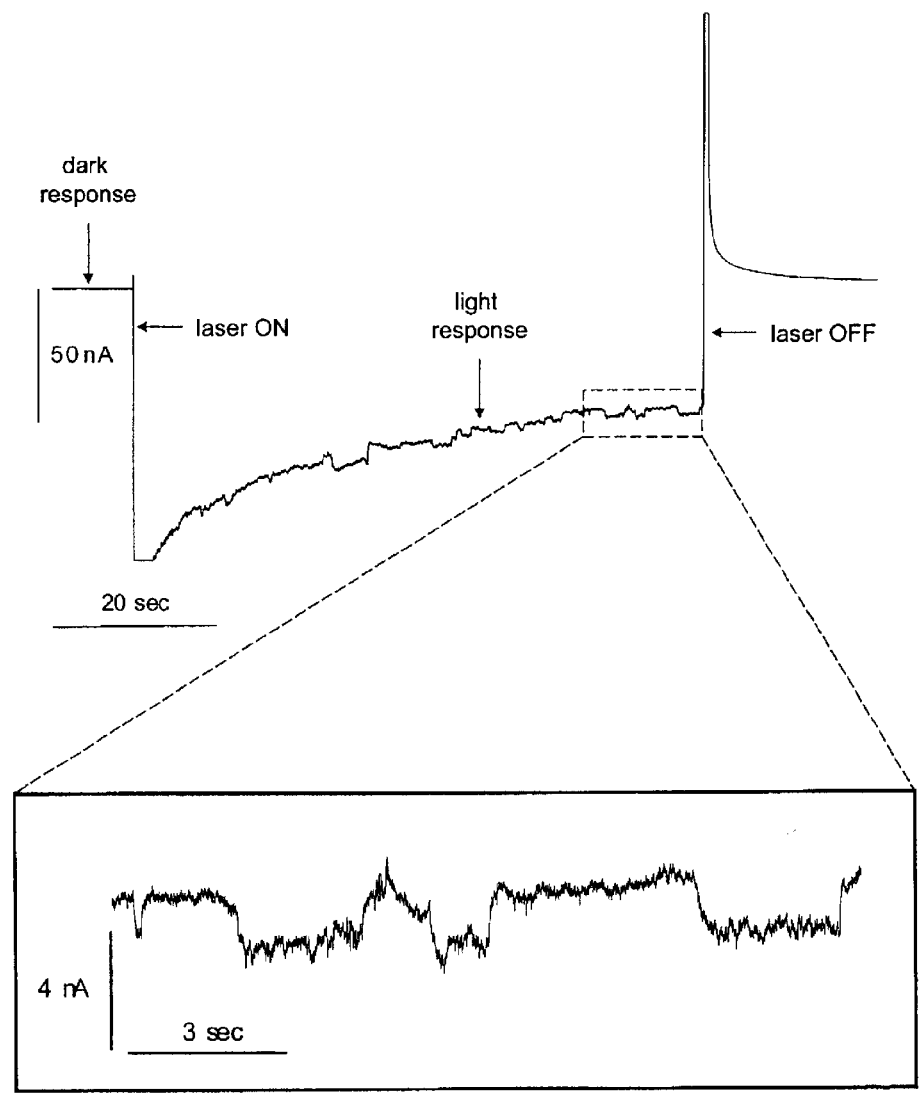
FIG. 4 shows ion channel responses driven by light-generated voltage, according to an example embodiment of the present invention.

FIG. 4 is a graph showing ion channel responses generated according to an example embodiment of the method and apparatus of the present invention. A silicon mesopore wafer coated with an amphotericin B membrane is illuminated with a 635 nm laser diode, generating a potential (approx. 160 mV) capable of driving ions through ion channels in the membrane. Distinct current levels are observed for open and closed channels.

While the invention has been described with reference to preferred and example embodiments, it will be understood by those skilled in the art that a number of modifications, additions and deletions are within the scope of the invention, as defined by the following claims.

What is claimed is:

1. A method of generating a voltage across a membrane, said method comprising:
    applying a membrane to a semiconductive substrate;
    placing an electrolyte in contact with the portion of the substrate bearing the membrane; and
    illuminating at least a portion of the semiconductive substrate with a light source.

2. The method of claim 1, further comprising observing the presence or absence of an electrical current through the membrane to address at least one ion channel of the membrane.

3. The method of claim 1, wherein the step of illuminating at least a portion of the semiconductive substrate with a light source comprises illumination with a laser.

4. The method of claim 1, wherein the step of illuminating at least a portion of the semiconductive substrate with a light source comprises scanning multiple locations on the semiconductive substrate with the light source.

5. The method of claim 1, wherein the membrane is a biological membrane comprising at least one ion channel.

6. A method of observing channel opening events and addressing the topography of a membrane, said method comprising:
    providing a semiconductive substrate having a membrane deposited thereon in contact with an electrolytic solution to form a semiconductor/liquid interface;

scanning successive portions of the semiconductive substrate with a light source to generate an electrical charge gradient at a location on the semiconductor/liquid interface; and measuring an electrical current through the membrane.

7. The method of claim 6, wherein the step of scanning successive portions of the semiconductive substrate with a light source comprises scanning the semiconductive substrate with a laser.

8. The method of claim 6, further comprising recording the measured electrical current as a function of the location on the semiconductor/liquid interface.

9. The method of claim 8, further comprising analyzing the recorded electrical current as a function of the location on the semiconductor/liquid interface to determine a channel opening event.

10. The method of claim 6, wherein the membrane is a biological membrane comprising at least one ion channel.

11. An apparatus for generating a transmembrane voltage, comprising:

a semiconductive substrate having a surface for receiving a membrane thereon in contact with an electrolyte to form a semiconductor/electrolyte interface; and a light source for illuminating at least a portion of the semiconductive substrate.

12. The apparatus of claim 11, wherein the light source is a laser.

13. The apparatus of claim 11, further comprising means for scanning the light source across the semiconductive substrate to illuminate successive portions of the semiconductive substrate.

14. The apparatus of claim 11, further comprising at least one electrode for measuring an electrical current induced through a membrane applied to the semiconductive substrate.

15. The apparatus of claim 14, further comprising means for recording the measured electrical current as a function of a location of the illuminated portion of the semiconductive substrate.

16. The apparatus of claim 11, further comprising a computer for receiving and processing data related to a generated transmembrane voltage.

\* \* \* \* \*